United States Patent [19]

Puritch et al.

[11] Patent Number: 4,859,689

[45] Date of Patent: Aug. 22, 1989

[54] SYNERGISTIC FUNGICIDAL COMPOSITION COMPRISE A BENZIMIDAZOLE COMPOUND, AN ALKYL PYRIDINIUM SALT, AND A CARRIER AND THE USE THEREOF TO COMBAT FUNGI

[75] Inventors: George S. Puritch, Brentwood Bay; Edward S. Kondo, Orleans, both of Canada

[73] Assignee: Safer, Inc., Newton, Mass.

[21] Appl. No.: 925,180

[22] Filed: Oct. 31, 1986

[51] Int. Cl.⁴ .................. A01N 43/40; A01N 43/52; A01N 47/30

[52] U.S. Cl. ........................... 514/358; 514/365; 514/388; 514/397; 546/272; 546/331; 548/205; 548/305; 560/16

[58] Field of Search .................. 514/358, 388, 365, 397

[56] References Cited

U.S. PATENT DOCUMENTS

| | | | |
|---|---|---|---|
| 3,370,957 | 2/1968 | Wagner et al. | 514/365 X |
| 3,377,239 | 4/1968 | Holan et al. | 514/365 |
| 3,687,966 | 8/1972 | Haubein | 260/309.5 |
| 3,930,010 | 12/1975 | Klopping | 424/273 |
| 4,028,464 | 6/1977 | Bell et al. | 424/273 |
| 4,044,145 | 8/1977 | Lacroix | 424/273 |
| 4,060,624 | 11/1977 | Klopping | 424/273 |
| 4,060,625 | 11/1977 | Klopping | 424/273 |
| 4,078,070 | 3/1978 | Albrecht et al. | 424/273 |
| 4,105,775 | 8/1978 | Albrecht et al. | 424/273 |
| 4,107,318 | 8/1978 | Albrecht et al. | 424/273 |
| 4,160,029 | 7/1979 | Duyfjes | 514/365 X |
| 4,164,582 | 8/1979 | Harju-Jeanty | 424/273 |
| 4,241,083 | 12/1980 | Morikawa et al. | 424/309 |
| 4,576,950 | 3/1986 | Puritch et al. | 514/358 |

FOREIGN PATENT DOCUMENTS 59-212405 12/1984 Japan .................. 514/365

Primary Examiner—Floyd D. Higel
Attorney, Agent, or Firm—Lahive & Cockfield

[57] ABSTRACT

There is disclosed a fungicidal composition comprising (A) a fungicidal compound selected from the group consisting of (i) benzimidazole compounds of the formula

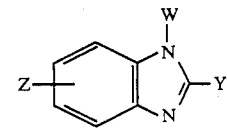

wherein W is H, or alkyl carbamoyl; Y is thiazolyl, dihydrothiazolyl, tetrahydrothiazolyl or furyl; Z is H, halogen or alkyl and (ii) benzimidazole related compounds of the formula

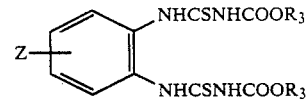

wherein $R_3$ is $C_{1-2}$ alkyl, and Z is as defined above, and (B) a synergist alkyl pyridinium salt of the formula

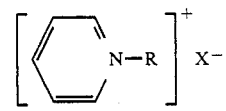

wherein R is an alkyl containing 8 to 20 carbon atoms; and X is a monovalent anion.

21 Claims, No Drawings

SYNERGISTIC FUNGICIDAL COMPOSITION COMPRISE A BENZIMIDAZOLE COMPOUND, AN ALKYL PYRIDINIUM SALT, AND A CARRIER AND THE USE THEREOF TO COMBAT FUNGI

FIELD OF THE INVENTION

This application closely relates to U.S. Pat. No. 4,576,950 issued on Mar. 18, 1986 and was assigned to the same assignee as this application.

This invention relates to a fungicidal composition based on the synergistic combination of alkyl pyridinium compounds with benzimidazole compounds or benzimidazole-related compounds. This combination provides increased effectiveness and activity against benzimidazole-tolerant fungi.

INFORMATION DISCLOSURE STATEMENT

The benzimidazole fungicides are used throughout the world including benomyl, carbendazim, thiabendazole, fuberidazole and thiophanate methyl. These compounds can control a variety of fungal pathogens on vegetables, fruits and trees, including grey mould (*Botrytis cinerea* Pers.), powdery mildews (*Erisyphe, Sphaerotheca*), Dutch Elm Disease (*Ceratocystis ulmi*), brown rot (*Monilinia fructicola*), etc. Unfortunately, the fungicidal effectiveness of the benzimidazoles has been significantly reduced due to the development of resistant fungal strains. The cause of this resistance has been attributed to a lack of penetration of the benzimidazoles through the outer fungal membranes (See Gessler, Phytopath. Z., 85: 35–38 (1976)).

A combination of some particular benzimidazole fungicides and surfactants is known in the art, for example, U.S. Pat. No. 3,930,010 to H.L. Klopping. This patent teaches that the fungicidal activity of a lower alkyl benzimidazol-2-yl carbamate compound is improved by the combination with a certain kind of surfactant at or above its critical micelle concentration (CMC). Those surfactants which were tested include nonionic, anionic and amphoteric surfactants, but no cationic surfactants were tested.

Accordingly an object of the present invention is to provide a fungicidal composition containing as the main ingredient a fungicidal benzimidazole or benzimidazole-related compound, the activity of which is increased by the addition of a synergist.

Another object of the present invention is to provide a method of combatting fungi employing a fungicidal benzimidazole or benzimidazole-related compound, the effectiveness of which is enhanced by the addition of a synergist against fungi including benzimidazole-susceptible as well as benzimidazole-tolerant or - resistant fungi.

Still another object of the present invention is to provide a method for restoring or recovering the fungicidal activity of the benzimidazole fungicide against benzimidazole-tolerant or - resistant fungi.

These and other objects of the present invention will be apparent to the person skilled in the art from the subsequent detailed description of the invention.

It has now been found that the mixture of benzimidazoles with alkyl pyridinium salts provides a unique combination that eliminates the fungal resistance factor and substantially improves the effectiveness of the fungicidal activity of the benzimidazole compounds, even at a concentration of the alkyl pyridinium salts far below its critical micelle concentration (CMC) level.

SUMMARY OF THE INVENTION

The present invention provides a fungicidal composition comprising: A. a fungicidal amount of (i) a benzimidazole compound of the following general formula:

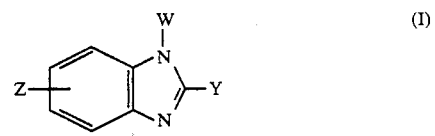

wherein

W represents a hydrogen atom or a lower alkyl carbamoyl group,

Y represents a thiazolyl, dihydrothiazolyl, tetrahydrothiazolyl or furyl group and, Z represents a hydrogen or halogen atom or a lower alkyl group, or an acid addition salt of the compound of formula (I), or (ii) a benzimidazole-related compound of the formula:

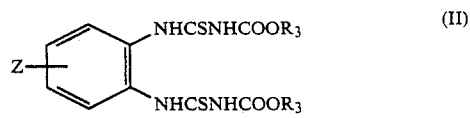

wherein $R_3$ represents a $C_{1-2}$ alkyl group, and

Z represents a hydrogen or halogen atom or a lower alkyl group, and

B. an alkyl pyridinium salt of the general formula:

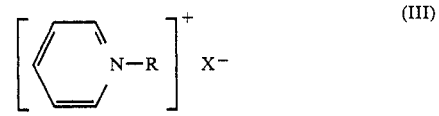

wherein R represents an alkyl radical containing 8 to 20 carbon atoms and $X^-$ represents a monovalent anion, in an amount sufficient to enhance the effectiveness of the fungicidal activity of the above benzimidazole compound, and a carrier.

An embodiment of the invention provides a method of combatting fungi, which comprises applying a fungicidally effective amount of a benzimidazole compound of formula (I) or a benzimidazole-related compound of formula (II) and an alkyl pyridinium salt of formula (III) in an amount sufficient to enhance the effectiveness of the fungicidal activity of the benzimidazole compound to fungi or habitats thereof.

Still another embodiment of the invention provides a method of restoring or recovering the fungicidal activity of the benzimidazole or benzimidazole-related fungicide against fungi which has acquired tolerance or resistance to such fungicide, which method comprises adding an effective amount of an alkyl pyridinium salt of formula (III) to a benzimidazole compound of formula (I) or a benzimidazole-related compound of formula (II).

DETAILED DESCRIPTION OF THE INVENTION

In the above formula (I) or (II),

"a lower alkyl carbamoyl" means a carbamoyl radical with an alkyl group having 1 to 6 carbon atoms of the formula —CONH—$R^1$ wherein $R^1$ represents an alkyl group, for example, methyl carbamoyl, ethyl carbamoyl, n-butyl carbamoyl and n-hexyl carbamoyl radicals;

"halogen atoms" include chlorine, bromine and iodine;

"a lower alkyl radical" means an alkyl radical having 1 to 4 carbon atoms such as methyl, ethyl and propyl radicals.

The radical Y may be a thiazolyl group, for example thiazol-2-, 4- or 5-yl group, a dihydrothiazolyl group, for example, 2,3-dihydrothiazol-2-, 3-, 4- or 5-yl group, and 4,5-dihydrothiazol-2-, 4- or 5-yl group, a tetrahydrothiazolyl group, for example, tetrahydrothiazol-2-, 3-, 4- or 5-yl group or a furyl group, for example, 2-furyl.

"Acid addition salts" of the compound of formula (I) include, for example, sulfuric acid, phosphoric acid, nitric acid, hydrochloric acid, p-toluene sulfonic acid and acetic acid salts.

Preferred benzimidazole compounds of formula (I) include those wherein W and Z are a hydrogen atom and Y is a thiazole or furyl group.

A compound of formula (I) wherein W is a hydrogen atom, Y is thiazol-4-yl and Z is a hydrogen atom, i.e., 2-(thiazol-4'-yl)benzimidazole is called "thiabendazole" in the industry and is commercially available.

A compound of formula (I) wherein W is a hydrogen atom, Y is 2-furyl and Z is a hydrogen atom, i.e., 2-(2'-furyl)benzimidazole is called "fuberiidazole" in the industry and is commercially available.

In the above formula (II), $R_3$ can be either methyl or ethyl.

Though from the chemical structure itself, the compounds of formula (II) may not be considered relating to the benzimidazole compounds (I), it is recognized in the art that the compounds (II) are related to benzimidazole fungicides because the former undergo decomposition and rearrangement within the crop plant to give rise to a benzimidazole compound.

A particularly preferred compound under this category is a compound of formula (II) wherein Z is hydrogen and $R_3$ is methyl, i.e., 1,2-bis(3'-methoxy-carbonyl-2'-thioureido)benzene, which is called "thiophanate-methyl" in the industry and is commercially available.

In the above formula (III), R may be any alkyl radical containing 8 to 20 carbon atoms including decyl, dodecyl, tetradecyl, hexadecyl, octadecyl and eicosyl. These alkyl radicals may be derived from natural sources, for example from coconut oil, beef tallow oil or palm oil or from synthetic alcohols, for example Ziegler alcohols or Oxo alcohols. They may comprise a mixture containing the pyridinium salts with various carbon atoms. The pyridinium salt may contain, in addition to the alkyl pyridinium salt, alkenyl pyridinium salts such as oleyl pyridinium salt. Preferred pyridinium salts have an alkyl radical with 12 to 18 carbon atoms, especially dodecyl, tetradecyl or hexadecyl radical. X may be any suitable monovalent anion including a halide, for example, chloride or bromide; a sulfonic acid residue, for example, methane sulfonate, benzene sulfonate or p-toluene sulfonate (tosylate) group; a sulfate acid residue, for example methyl sulfate, ethyl sulfate; and acetate. The most preferred is dodecyl (lauryl) pyridinium chloride or bromide.

The ratio of the two components in the composition may vary widely range so far as the fungicidal activity of the benzimidazole(-related) compound is enhanced. Preferably about 0.1 to 10 parts by weight of the alkyl pyridinium salt is incorporated in the composition or used in the field per part of the benzimidazole(-related) compound, and more preferably about ⅓ to 3 parts by weight of the pyridinium salt is used.

The composition of the invention may be in any suitable form for the fungicidal composition with a suitable carrier. It may be in a customary formulation, such as wettable powders, concentrated solutions, granules, emulsions and suspensions. These formulations may be prepared in known manner, for example by mixing the active compounds with carriers, optionally with the use of surface active agents (or emulsifying agents) which are compatible with the alkyl pyridinium salts. As a liquid carrier there may be mentioned water, an organic solvent such as aromatic hydrocarbons, chlorinated hydrocarbons, aliphatic or alicyclic hydrocarbons, alcohols, ketones, ethers and esters. As a solid carrier there may be mentioned ground natural minerals such as kaolins, clays, talc, chalk, quartz and diatomaceous earth and group synthetic minerals such as highly-dispersed silicic acid, alumina and silicates. As an emulsifying agent there may be mentioned non-ionic emulsifiers such as polyoxyethylene fatty alcohol ethers, polyoxyethylene alkyl phenol ethers and polyoxyethylene fatty acid esters. The formulation normally contains from 0.1 to 90, preferably from 1 to 50%, more preferably from 5 to 30%, by weight of the active ingredient the (benzimidazole or benzimidazole-related compound).

According to the invention, the fungicidal benzimidazole(-related) compound and the alkyl pyridinium salt may be applied to fungi or habitat thereof in a usual manner. The active compound may be used in the form of the formulations commercially available or in the use form further diluted from the formulations. The active benzimidazole(-related) compound content of the use form can vary within wide ranges, the preferred use form content is from 0.1 ppm to 100,000 ppm more preferred content is from 1 to 1,000 ppm and further preferred content is from 10 to 200 ppm. The amount of the active compound to be applied per unit area also varies depending on various conditions, for example, the kind of fungi intended, the stage of the development of the plant, the kind of plant to be protected, the temperature, the humidity and so on. In general the active ingredient benzimidazole is applied 0.01 to 50 kg/ha, and preferably 0.1 to 10 kg/ha.

The following examples illustrate the invention, however these examples should not be regarded as limiting the invention.

Preparation

The alkyl pyridinium salts used in the following examples were synthesized by direct N-alkylation of the pyridine with the desired alkyl compound. The reaction is carried out with the addition of the alkyl chloride to an excess of pyridine and heating the reaction mixture to a temperature between 40° C. and the reflux point, for a length of time between 2 hours and 48 hours, depending on the alkyl reagent used. The product is purified by repeated recrystallizations from acetone or alcohol/ether solutions.

The benzimidazole(-related) compounds were obtained commercially or synthesized.

EXAMPLE 1

The effects of dodecyl pyridinium chloride in combination with thiabendazole were studied on the conidia of *Botrytis cinerea*.

The fungicidal activities of dodecyl pyridinium chloride and thiabendazole were measured on the conidia of a benzimidazole-tolerant strain of *Botrytis cinerea*. The test was designed to assess the fungicidal activity of the alkyl pyridinium alone and of thiabendazole alone and in their combinations and was replicated five times. Compounds were incorporated into cooled, autoclaved 2% PDA (potato dextrose agar) medium and the medium was poured into 9 cm sterile petri dishes. Conidia were dispersed on the surface of the cooled agar and the amount of germination was measured after 18 hours incubation at 8° C. Results are shown in Table I below.

TABLE I

Germination (%) of conidia of benzimidazole-tolerant strains of *Botrytis cinerea* on 2% PDA

| Treatment (ppm) | Mean germination (%) Strain 6 | Strain 9 |
| --- | --- | --- |
| Control | 94.2 ± 1.3 | 89.8 ± 3.1 |
| 25 APS12C* | 86.8 ± 1.6 | 64.4 ± 5.7 |
| 25 thiabendazole | 91.6 ± 1.8 | 83.4 ± 3.4 |
| 25 APS12C/25 thiabendazole | 58.4 ± 3.8 | 40.4 ± 5.3 |
| 50 APS12C | 60.4 ± 3.2 | 34.8 ± 3.8 |
| 50 thiabendazole | 85.8 ± 4.4 | 89.0 ± 2.2 |
| 50 APS12C/50 thiabendazole | 7.4 ± 1.5 | 1.2 ± 1.1 |

*APS12C = dodecyl pyridinium chloride

The expected reductions in germination over controls for 50 ppm APS12C/50 ppm thiabendazole, based on additive affects of each used alone, were 44.8% and 62.2% for strains 6 and 9, respectively. The observed values were 92.1% and 98.7%.

Similar effects were seen for both strains at concentrations 25 ppm ASP12/25 ppm thiabendazole.

The CMC (critical micelle concentration) value for APS12C is reported to be 3.89 (log ppm) (c.f. Mukerjee, P. and K.J. Mysels, 1971. Critical Micelle Concentrations of Aqueous Surfactant System, United States Department of Commerce, NSRDS-NBS 36. Washington, D.C. pp. 222), that is a little less than 1000 ppm. From above Table I, it will be apparent that the alkyl pyridinium compound at a concentration far below its CMC value synergistically increases the fungicidal activity of the benzimidazole compound against the benzimidazole-tolerant fungus.

EXAMPLE 2

Dodecyl pyridinium chloride was tested alone and in combination with thiophanate methyl against the conidia of two benzimidazole-tolerant strains of Botrytis cinerea. Test compounds were incorporated into 2% PDA and the conidia dispersed over the surface. The plates were incubated 14 h. at 14° C. and five replicates of 100 conidia each per treatment were assessed for germination.

The results are shown in Table II below

TABLE II

Germination of conidia of 2 benzimidazole-tolerant strains of *Botrytis cinerea* on 2% PDA.

| Treatment (ppm) | Mean germinated (%) Strain 1 | Strain 2 |
| --- | --- | --- |
| Control | 98.0 ± 2.0 | 89.2 ± 2.6 |
| 50 APS12C* | 55.0 ± 8.9 | 27.0 ± 4.8 |
| 50 Thiophanate methyl | 97.2 ± 1.8 | 84.8 ± 6.8 |
| 50 APS12C plus 50 Thiophanate methyl | 18.6 ± 5.8 | 6.4 ± 1.5 |

*APS12C = dodecyl pyridinium chloride.

Results showed that germination of conidia for the first benzimidazole-tolerant strain at 50 ppm APS12C plus 50 ppm thiophanate methyl was decreased by 81.0% from control germination, while the expected reduction through additive effects would have been 44.6% (Table II). A similar effect was seen for a second benzimidazole-tolerant strain of B.cinerea.

What we claim as our invention is:

1. A fungicidal composition comprising: A) a fungicidal amount of (i) a benzimidazole compound of the following formula:

wherein
W represents a hydrogen or lower alkyl carbamoyl
Y represents a thiazolyl, dihydrothiazolyl, tetrahydrothiazolyl or furyl group, and
Z represents hydrogen or halogen or a lower alkyl, or an acid addition salt of the benzimidazole compound or (ii) a benzimidazole-related compound of the formula:

wherein $R_3$ represents $C_{1-2}$ aklyl, and
Z represents a hydrogen or halogen atom or a lower alkyl group, and B) an alkyl pyridinium salt of the formula:

wherein R represents alkyl containing 8 to 20 carbon atoms and $X^-$ represents a monovalent anion in an amount sufficient to enhance the effectivenes of the fungicidal activity of said benzimidazole compound, and a carrier.

2. The composition according to claim 1, which contains 0.1 to 90% by weight of the fungicidal compound (A) and 0.1 to 10 parts by weight of the alkyl pyridinium compound (B) per part of the fungicidal compound (A).

3. The composition according to claim 2 having a benzimidazole compound in which W is hydrogen, Y is a thiazolyl or furyl group, and Z is hydrogen.

4. The composition according to claim 2 having a benzimidazole-related compound in which Z is a hydrogen.

5. The composition according to claim 2 having an alkyl pyridinium salt in which R is an alkyl with 12 to 18 carbon atoms and X is chloride or bromide.

6. The composition according to claim 5, wherein the fungicidal compound (A) is thiabendazole.

7. The composition according to claim 5, wherein the fungicidal compound (A) is thiaphanate-methyl.

8. The composition according to claim 4, which contains 1 to 50% by weight of the fungicidal compound (A).

9. The composition according to claim 4 which contains 5 to 30% by weight of the fungicidal compound (A).

10. A method of combatting fungi, which comprises applying to fungi or habitats thereof,
(A) a fungicidally effective amount of (i) a benzimidazole compound of the formula

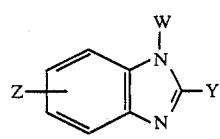

wherein
W represents a hydrogen or a lower alkyl carbamoyl,
Y represents a thiazolyl, dihydrothiazolyl, tetrahydrothiazolyl or furyl group, and
Z represents hydrogen or halogen or a lower alkyl radical, or an acid addition salt of the benzimidazole compound or (ii) a benzimidazole-related compound of the formula:

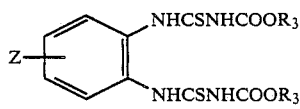

wherein
$R_3$ represents a $C_{1-2}$ alkyl, and
Z represents hydrogen or halogen or a lower alkyl, and
B) an alkyl pyridinium salt of the formula

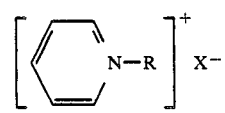

wherein R represents alkyl containing 8 to 20 carbon atoms and $X^-$ represents a monovalent anion in an amount sufficient to enhance the effectiveness of the fungicidal activity of said fungicidal component (A).

11. The method according to claim 10, wherein the compounds are applied in a diluted form containing from 0.1 to 100,000 ppm of the fungicidal compound (A).

12. The method according to claim 11, wherein the dilution contains 0.1 to 10 parts by weight of the alkyl pyridinium salt (B) per part of the fungicidal compound (A).

13. The method according to claim 10, wherein the fungicidal compound (A) is applied in an amount of 0.1 to 10 kg/ha.

14. The method according to claim 11, 12 or 13, which employs as the component (A) a benzimidazole compound wherein W is hydrogen, Y is a thiazolyl or furyl group and Z is hydrogen.

15. The method according to claim 11, wherein the fungicidal compound (A) is thiabendazole.

16. The method according to claim 11, wherein the fungicidal compound (A) is thiophenate-methyl.

17. A method according to claim 10, wherein the fungi are benzimidazole-tolerant or -resistant fungi.

18. A method for restoring or recovering the fungicidal activity of a benzimidazole or benzimidazole-related fungicide against fungi which are tolerant or resistant to such fungicides, which method comprises incorporating (A) 0.1 to 10 parts by weight of an alkyl pyridinium compound of the formula:

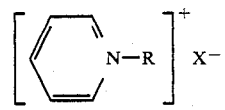

wherein R represents alkyl containing 8 to 20 carbon atoms and $X^-$ represents a monovalent anion with (A) one part by weight of a fungicide selected from (i) a benzimidazole compound of the formula:

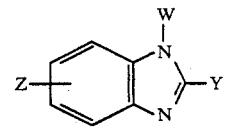

wherein
W represents a hydrogen or a lower alkyl carbamoyl,
Y represents thiazolyl, dihydrothiazolyl, tetrahydrothiazolyl or furyl group, and
Z represents hydrogen or halogen or a lower alkyl radical or, an acid addition salt of the benzimidazole compound and (ii) a benzimidazole-related compound of the formula:

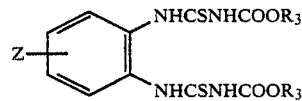

wherein
$R_3$ represents a $C_{1-2}$ alkyl, and
Z represents a hydrogen or halogen or lower alkyl.

19. The method according to claim 18, wherein the fungicidal compound (A) is thiabendazole.

20. The method according to claim 18, wherein the fungicidal compound (A) is thiaphanate-methyl.

21. The method according to claim 18, 19 or 20, wherein in the alkyl pyridinium compound, R is an alkyl with 12 to 18 carbon atoms and $X^-$ is chloride or bromide.

* * * * *